US012073944B2

(12) United States Patent
Paineau et al.

(10) Patent No.: US 12,073,944 B2
(45) Date of Patent: Aug. 27, 2024

(54) METHOD AND SYSTEM FOR CHARACTERIZING STOOL PATTERNS OF YOUNG INFANTS (71) Applicant: N.V. Nutricia, Zoetermeer (NL)

(72) Inventors: Damien Luc Dominique Marie Paineau, Singapore (SG); Agathe Camille Foussat, Singapore (SG); Thomas Ludwig, Singapore (SG); Inès Oukid, Paris (FR)

(73) Assignee: N.V. Nutricia, Zoetermeer (NL)

(*) Notice: Subject to any disclaimer, the term of this patent is extended or adjusted under 35 U.S.C. 154(b) by 745 days.

(21) Appl. No.: 17/253,130

(22) PCT Filed: May 28, 2019

(86) PCT No.: PCT/NL2019/050310
§ 371 (c)(1),
(2) Date: Dec. 17, 2020

(87) PCT Pub. No.: WO2019/245360
PCT Pub. Date: Dec. 26, 2019

(65) Prior Publication Data
US 2021/0265059 A1 Aug. 26, 2021

(51) Int. Cl.
G16H 50/20 (2018.01)
A61B 5/00 (2006.01)
(Continued)

(52) U.S. Cl.
CPC .......... G16H 50/20 (2018.01); A61B 5/0013 (2013.01); A61B 5/0022 (2013.01);
(Continued)

(58) Field of Classification Search
CPC ...... G16H 50/20; G16H 50/30; A61B 5/0013; A61B 5/0022; A61B 5/0077; A61B 5/48;
(Continued)

(56) References Cited

U.S. PATENT DOCUMENTS 10,402,697 B2    9/2019   Yang et al.
2005/0270483 A1 12/2005  Fujimatsu et al.
(Continued)

FOREIGN PATENT DOCUMENTS

CN    104376193 A    2/2015
CN    105654469 A    6/2016
CN    107492099 A    12/2017

OTHER PUBLICATIONS

Yvan Vandenplas et al: "Development of the Brussels Infant and Toddler Stool Scale ('BITSS'): protocol of the study", BMJ Open, vol. 7, No. 3, Mar. 1, 2017 (Mar. 1, 2017).
(Continued)

Primary Examiner — Brandon J Miller
(74) Attorney, Agent, or Firm — N.V. Nederlandsch Octrooibureau (57) ABSTRACT The invention provides a method of analysing the consistency of stool, including the steps of: providing stool of an infant, capturing, with a portable device comprising a camera, an image of the stool, providing the captured image to an input layer of a pre-trained convolutional neural network, CNN, processing the captured image using the CNN to obtain, from a final layer of the CNN, a classification vector and to obtain information about a predicted score from the classification vector, wherein at least the final layer of the CNN has been customized so that each element of the classification vector corresponds to a score of a stool analysis scale, and storing information about the predicted store.

20 Claims, 3 Drawing Sheets (51) Int. Cl.
*G06T 7/00* (2017.01)
*G16H 50/30* (2018.01)

(52) U.S. Cl.
CPC .............. *A61B 5/0077* (2013.01); *A61B 5/48* (2013.01); *A61B 5/7267* (2013.01); *A61B 5/742* (2013.01); *G06T 7/0012* (2013.01); *G16H 50/30* (2018.01); *G06T 2207/10024* (2013.01); *G06T 2207/20084* (2013.01); *G06T 2207/30004* (2013.01)

(58) Field of Classification Search
CPC ..... A61B 5/7267; A61B 5/742; G06T 7/0012; G06T 2207/10024; G06T 2207/20084; G06T 2207/30004; G06T 7/0004
See application file for complete search history.

(56) References Cited

U.S. PATENT DOCUMENTS

| | | |
|---|---|---|
| 2008/0298796 A1 | 12/2008 | Kuberka et al. |
| 2017/0046613 A1 | 2/2017 | Paluri et al. |
| 2018/0157939 A1 | 6/2018 | Butt et al. |
| 2019/0272631 A1* | 9/2019 | Shemonski ............ A61B 3/102 |
| 2020/0357516 A1* | 11/2020 | Kirby ..................... G16H 40/60 |

OTHER PUBLICATIONS

Abadi et al.: "TensorFlow: A System for Large-Scale Machine Learning", 12th USENIX Symposium on Operating Systems Design and Implementation, 2016.

* cited by examiner

METHOD AND SYSTEM FOR CHARACTERIZING STOOL PATTERNS OF YOUNG INFANTS

FIELD OF THE INVENTION

The present invention relates to a method and a system for analyzing the consistency of a stool sample.

BACKGROUND ART

The healthcare of an infant is the most important task for a parent. Advances in technology allow helping parents and caregivers with the task of tracking the development of the babies and quickly detecting certain anomalies. When it comes to the nutrition of the infant, it is important to detect whether there are anomalies in the digestive system, or whether the infant's body is absorbing all the nutrients it needs to.

For assessing the performance of the digestive system, analyzing the stool pattern is known to provide good insights. Scales to compare stools with a set of stool analysis scale scores help to classify the type of stool and to retrieve conclusions from there. Examples of such scales are the Bristol Stool Form Scale (BSS) and the Amsterdam Stool Scale. The BSS, which consists of seven images of different stool consistencies, allows assessment of stool consistency (scale 1 for hard lumps to scale 7 for watery stools), in an objective manner in adults. The BSS may also be used to characterize the stool of infants and young children.

When parents visit health care professionals (HCPs) because they are concerned about the wellbeing of their infants, HCPs usually ask questions about the consistency of the stool of the infants, and these questions are difficult to answer for most parents. When parents are asked to keep a log of the stool consistency of their infants, it is difficult for them to identify the stool consistency and the associated stool analysis scale score that fits a stool of their kids.

It would be desirable to have a system where parents and caregivers could keep track of the stool pattern, i.e. stool consistency, frequency and colour, of their babies in real time. It would further be desirable, that irrespective of which caregiver (parent, grandparent, nanny or day care) is changing the diaper, or helping the child to use a potty or toilet chair, the stool pattern is tracked in an objective and consistent manner. It would also be desirable to have a system that, based on the observed stool patterns, provides an indication, either that everything is normal, which would provide ease of mind to the parents and caregivers, or that the infant's stool pattern is not behaving as expected and that is advisable to visit an HCP.

Nowadays, with the habit of people carrying their smartphones, tablet computers or other portable devices with them continuously, there is an effort to provide mobile applications (apps) to be executed by these portable devices that can make normal life tasks easier for the users. Furthermore, the procedure of taking photos of the infant in order to see its development is a common practice for parents, by means of which they can approximately see how the infant is growing.

This can also be applied to keeping track of stool patterns. Programs or apps are known which allow to introduce or to capture images of stool and manually select a score of a stool analysis scale that better suits the stool on the image, in order to keep a log of the digestive system performance throughout time. Also programs or apps are known which allow the use of colour recognition techniques to automatically detect the colour of stool.

Although these apps may help parents and caregivers analyse some characteristics of the stool of their babies, it is sometimes difficult to manually make a classification, and it is tedious to manually keep a log, and thus there is a need for a method to more accurately analyse characteristics of stool of an infant, in a manner that is easy for the parents or caregivers, and that yet provides an accurate and fast classification.

SUMMARY OF THE INVENTION

The invention provides a method of analysing the consistency of stool, comprising the steps of: providing stool of an infant, capturing, with a portable device comprising a camera, an image of the stool, providing the captured image to an input layer of a pre-trained convolutional neural network, CNN, processing the captured image using the CNN to obtain, from a final layer of the CNN, a classification vector and to obtain information about a predicted score from the classification vector, wherein at least the final layer of the CNN has been customized so that each element of the classification vector corresponds to a respective score of a stool analysis scale, and storing information about the predicted score.

The invention thus provides a method for characterizing infant stool, which is easy to implement and yet provides fast and accurate classification results. The use of a CNN to classify the stool provides an increased accuracy in the classification results, and the use of a camera of a portable device for capturing the image allows to simplify the task for the parents or caregivers, because it may be as simple as to capture an image of the stool and automatically receive the results, without having to further manipulate the stool. In addition, there is no inter-observer variability, because independently of who captures the image, the results will be provided in an objective way.

In an embodiment according to the invention, the stool is provided in an open diaper. This allows to simplify the task for parents and caregivers, because the image can be captured directly from the diaper on which the stool has been deposited, and while changing the infant the image can easily be captured before disposing the diaper.

In an embodiment according to the invention, the stool is provided in a potty, a bed pan, a toilet chair, or a toilet with plateaus. The invention can thus facilitate the task for parents and caregivers, who do not need to manipulate the stool, as the image may be captured directly at the place where it has been deposited by the infant, adapting to the possible different situations.

In an embodiment according to the invention, the method further comprises displaying, by the portable device, guiding information to meet predetermined conditions before capturing the image. This can help the user of the portable device, which may be for example a parent, another family member or a caregiver, capture an image which has optimal characteristics to be used in the classification step.

In an embodiment according to the invention, capturing the image comprises automatically capturing the image by the portable device when predetermined conditions are met.

In an embodiment according to the invention, the predetermined conditions comprise a condition that the stool is placed on a surface with a regular background. A regular background may be a background having a specific pattern, a uniform background, and the like. In an embodiment according to the invention, the predetermined conditions comprise a condition that the stool is the only object present in the image.

If the stool is provided in an open diaper, in an embodiment according to the invention, the predetermined conditions comprise a condition that the diaper is placed on a surface with a regular background, and in an embodiment according to the invention, the predetermined conditions comprise a condition that the diaper is the only object present in the image.

In an embodiment according to the invention, the information about the predicted score comprises at least one of the predicted score, the captured image of the stool, and the date and/or the time at which the image was captured. The information may also comprise other types of information that are useful for the parents and caregivers or to the app, such as whether the colour of the stool is considered normal or not.

In an embodiment according to the invention, processing the captured image using the CNN is performed by the portable device. In an embodiment according to the invention, processing the captured image using the CNN is performed by a server communicating with the portable device. In this second scenario, the portable device may send the captured image to a server which is in communication with the portable device via a network such as the Internet, and receive the classification vector or the predicted score from the server. This may be advantageous in a situation in which the portable device does not have enough computational power to perform all the operations that are required in the CNN. The first scenario, however, may be advantageous when the mobile device is not connected to a network, because it allows for an offline prediction of the score.

In an embodiment according to the invention, the information about the predicted score is stored in at least one of the portable device or a server communicating with the portable device. The server may be used to store all the information about the predicted score, and also to store the captured images, to release memory from the portable device, and to allow that for example HCPs can have access to the information, if desired. The portable device may also locally store copies of the captured images and the information (score) derived from it.

In an embodiment according to the invention, the image is a colour image. This allows the image to comprise more information (a third level of information) which can be used in the CNN to improve its performance. In an embodiment according to the invention, the method also comprises automatically detecting the colour of the stool from the captured image, and analysing it in order to provide information. This may allow the method to also provide information about whether the colour is normal or not, which together with the consistency, can allow for a better determination of possible anomalies.

In an embodiment according to the invention, the method further comprises analysing a frequency in which the stool is produced, based on stored time information related to the predicted scores for a plurality of captured images. By determining the frequency of occurrence from the number of images captured per day and the time when they were captured, frequency can be used to provide additional information, and also a combination of consistency and frequency can be used to provide information, e.g. for diarrhea (three or more watery stools per day), or constipation (two or less hard stools per week).

The invention further provides a system for analysing the consistency of stool, comprising: a portable device comprising: a camera configured to capture an image of stool of an infant, a controller configured to provide the captured image to an input layer of a pre-trained convolutional neural network, CNN, obtain from a final layer of the CNN, a classification vector, wherein at least the final layer of the CNN has been customized so that each element of the classification vector corresponds to a respective score of a stool analysis scale, and obtain information about a predicted score from the classification vector, and a memory for storing the information about the predicted score.

In an embodiment according to the invention, the stool is provided in an open diaper. In an embodiment according to the invention, the stool is provided in a potty, a bed pan, a toilet chair, or a toilet with plateaus.

In an embodiment according to the invention, the information about the predicted score comprises at least one of the predicted score, the captured image of the stool, and the date and/or time at which the image was captured.

In an embodiment according to the invention, the system further comprises a server for communicating with the portable device, wherein the server is configured to store the information about the predicted score.

In an embodiment according to the invention, processing the captured image using the CNN to obtain the classification vector from a final layer of the CNN is performed by the portable device.

In an embodiment according to the invention, the server is further configured to process the captured image using the CNN to obtain the classification vector from a final layer of the CNN, and the portable device is further configured to transmit the captured image to the server and to receive the predicted score from the server. In an embodiment, thus, the server may perform a decision on the most probable score among the possible scores of the stool analysis scale based on the classification vector, and send the score to the portable device.

In an embodiment according to the invention, the image is a colour image.

The invention further provides a computer program product for analysing the consistency of stool, comprising a computer readable medium comprising codes executable by at least one processor to execute a method according the invention.

BRIEF DESCRIPTION OF THE DRAWINGS

The present invention will be discussed in more detail below, with reference to the attached drawings, in which.

DESCRIPTION OF EMBODIMENTS

Figure 1:
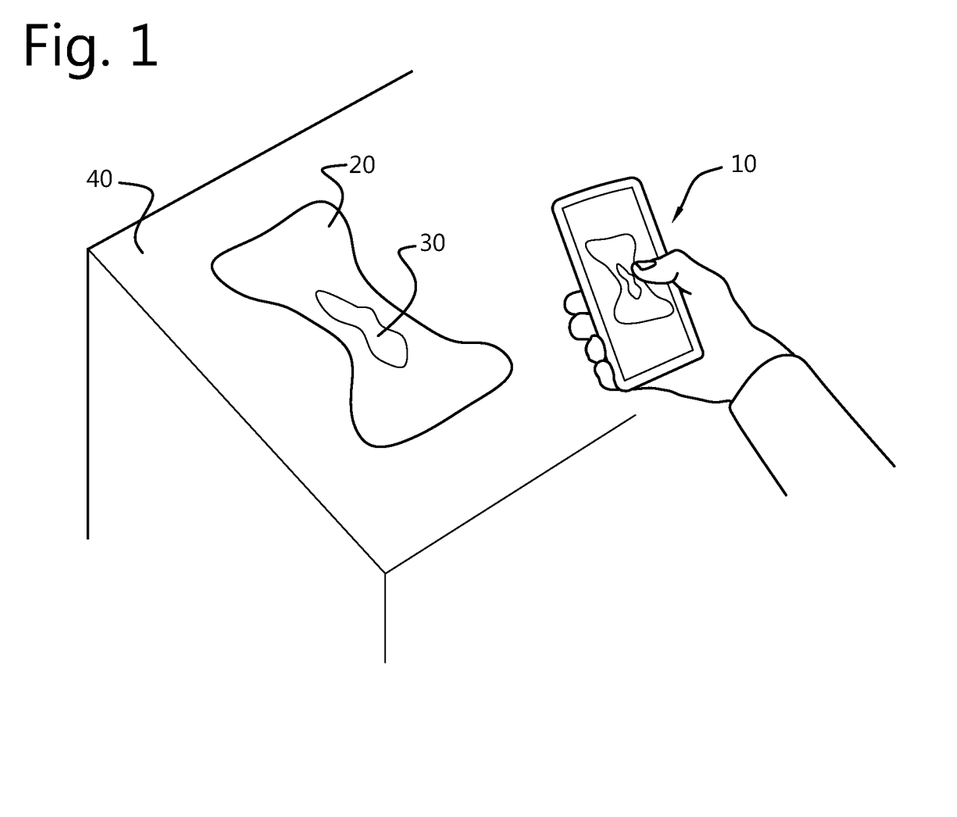
FIG. 1 depicts an overview of an embodiment of the present invention.

FIG. 1 depicts an overview of an embodiment of the present invention. Although embodiments of the present invention comprise stool being placed in a diaper, a potty, a bed pan, a toilet chair, a toilet with plateaus, or other similar locations, in the embodiment of FIG. 1, an example is depicted in which the stool is placed in a diaper. A diaper 20 comprising infant stool 30 is placed in an open position on a surface 40, and a portable device 10 is used by a user, to capture an image of the open diaper 20 with the stool 30. The captured image can be used by an app running on the portable device, and the app may input the captured image to a model comprising a CNN which will perform a series of operations in order to obtain a classification vector with probabilities of the possible scores in a stool analysis scale, and in order to obtain a predicted score based on the classification vector (i.e., the score with the highest probability). In order to obtain the best results from the classification process, it is desirable that the captured image has good characteristics, and therefore, that certain predetermined conditions are met. As an example of the conditions to be met, the stool 30 should be as recent as possible, so that its properties (colour, consistency) have not yet changed due to for instance that a part of the stool is absorbed by the diaper. The image should hence be captured shortly after the stool has been deposited, and in the embodiment of FIG. 1, shortly after the diaper 20 has been filled with stool, and a suitable period to capture the image is up to ten minutes from the time the diaper has been filled. The colour of the stool in the captured image may be also used, by the CNN or by a different algorithm, to provide additional information. The app of the portable device may automatically detect the colour of the stool from the captured image, and analyse it in order to provide information. This allows to also provide information related to whether the colour is normal or not, which together with the consistency, can allow for a better determination of possible anomalies.

Another example of a condition which should be met is that the image is captured with sufficient light to clearly distinguish the features in the image, but not with too much light as this may modify the real colour and appearance of the image features. An example of how this can be achieved is by using natural light (daylight) or light from a ceiling lamp. Using the flash of the camera is however less preferred, as it could change the appearance of the image.

Another example of a condition is that the background of the image should preferably be regular, such as following a pattern, or uniform. If the stool is placed in a potty, a bed bad a toilet chair, or a toilet with plateaus, it is desirable that the background is uniform. If the stool is placed in a diaper, as represented in the embodiment of FIG. 1, it is preferable that the diaper 20 is in the foreground of the image. A surface 40 of a table which is uniform is an example of a suitable background.

Another example of a condition that should be met is that no other object should be present in the image. If the stool is placed in a potty, a bed bad a toilet chair, or a toilet with plateaus, it is desirable that only the stool and the background are present in the image, no other objects or parts of a body. If the stool is placed on a diaper, it is desirable that no other object other than the diaper 20 containing the stool 30 is present. Parts of the baby's body, or other objects, should not be present in the image. If, however, the captured image has undesirable objects surrounding the stool, it may be possible to cut the captured image to eliminate the undesirable objects before the image is input to the CNN. Other pre-processing steps may be performed such as modifying the resolution of the captured image, changing the format of the image, or other steps to remove noise in the image.

It should be noted that embodiments of the invention may use only one of the predetermined conditions, or any combination of them. It should also be noted that other predetermined conditions can be used, as long as they help the user obtain an image which is suitable for being input to the CNN. Which predetermined conditions are to be used may be determined and modified in the settings of the app, or may be predefined, and a controller of the portable device may control which predetermined conditions are used, and how they are determined.

Figure 2A:
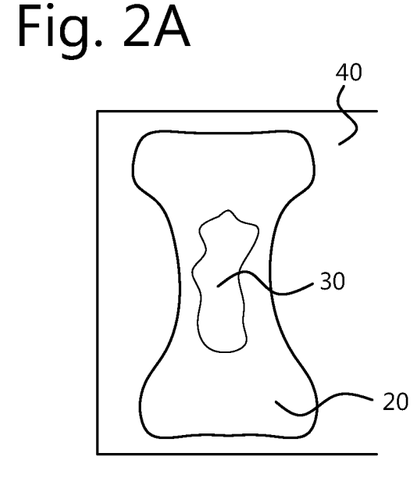
FIGS. 2a and 2b show different dispositions of a diaper comprising a stool according to the present invention.
Figure 2B:
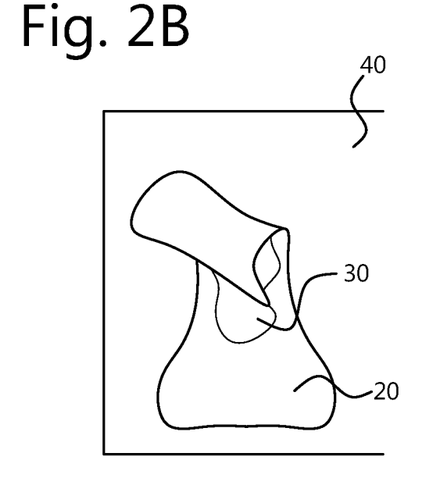

Other examples of conditions that should be met can be seen in FIGS. 2a and 2b, which show different dispositions of a diaper comprising a stool according to the present invention. Again, the example of a stool in a diaper is represented, but the skilled person will understand that the features may similarly be applied to other embodiments in which the stool is provided in a potty, a bed bad, a toilet chair, a toilet with plateaus, or the like. In FIG. 2a, an open diaper 20 comprising stool 30 can be seen, with a uniform background 40, which in this case corresponds to the top of a uniform-surface table. In FIG. 2a, no other objects other than the diaper are present in the image. An image like the one in FIG. 2a could be considered suitable for the method of the present invention.

According to an embodiment, the portable device 10, before capturing the image, for example before pointing the camera to the stool, or when the user is pointing the camera to the stool, may give indications to the user to remind him/her of some conditions that should be met (the light should be enough, and the like). These conditions may be some or all of the predetermined conditions described above, or different conditions. The portable device may additionally guide the user in order to bring the portable device 10 closer or further to the stool, in FIG. 2a, in the diaper 20, to change the angle or the light source in the room in order to achieve better light in the image, and so on, and provide an indication of when the image could be suitable. This may allow the user to capture an image which has good characteristics and will improve the success rate of the classification. According to an embodiment, the portable device 10 may automatically capture the image when it detects that the portable device 10 is located at a suitable distance from the stool, or the diaper 20, the light conditions are suitable, or when any other desirable condition is met. The condition or conditions to be met in order for the portable device to decide to automatically capture the image may be previously defined.

In FIG. 2b, the diaper 20 is not in a suitable position for capturing the image, as the diaper is not completely open and hence the stool 30 cannot be sufficiently identified. According to an embodiment of the invention, by seeing the guidance displayed in the portable device the user can be made aware that this is an unsuitable position and can open the diaper. According to another embodiment, the app will provide the guidance before pointing the camera to the stool, and the user will be aware that for example the diaper needs to be open, so that an image like the one represented in FIG. 2b is not captured.

Figure 3:
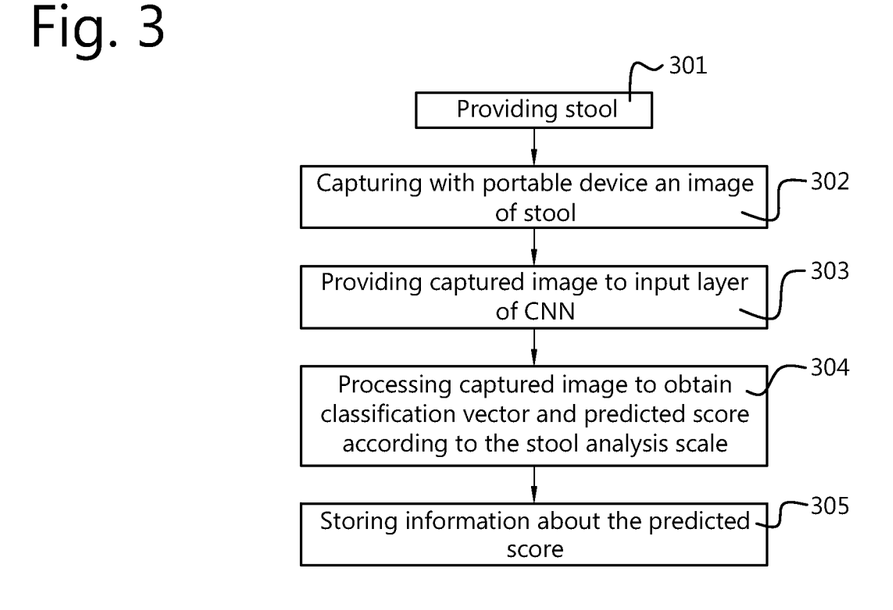
FIG. 3 shows a flow chart illustrating a method according to the present invention.

FIG. 3 shows a flow chart illustrating a method according to the present invention. In step 301, stool 30 is provided. As seen above, it can be provided in a diaper, which then will be open in order to capture the image, or in a potty, a bed bad, a toilet chair, or a toilet with plateaus. In step 302, an image of the stool 30 is captured by a camera comprised in the portable device 10. The capturing step may be performed by an app being run in the portable device 10, which the user may initialize.

In step 303, the captured image is provided to the input layer of a convolutional neural network (CNN). A CNN is a neural network suitable for classifying images, and unlike regular neural networks, the layers of a CNN have neurons arranged in three dimensions: width, height and depth. For the purposes of this disclosure, a CNN is understood to be a neural network, for example a feed-forward neural network, with multiple layers, comprising layers that transform an input 3D volume to an output 3D volume. In an embodiment, a CNN comprises an input and an output layer, with multiple hidden layers in between. Each of the hidden layers can be one of a convolutional layer, a pooling layer, a fully connected layer and a normalization layer. Such neural networks can for example be implemented using the TensorFlow library (Abadi et al "TensorFlow: A System for Large-Scale Machine Learning", 12th USENIX Symposium on Operating Systems Design and Implementation, 2016).

Throughout the layers of the CNN, the full input image, colour or grayscale, is reduced to a single vector of class scores, or classification vector. In the present invention, step 304 comprises processing the captured image to obtain a classification vector and a predicted score according to the stool analysis scale. The image captured with the portable device is the input image to the CNN, either in Red, Green, Blue colour or as a grayscale image. The output single vector is a classification vector comprising the probability values of each possible score. The predicted is score can be set to the score with the highest probability among the scores in the classification vector.

Several stool analysis scales can be used, for example the Bristol Stool Form Scale (BSS), the Amsterdam Stool Scale, or any other suitable scale, such as the Brussels Infant and Toddler Stool Scale (BITSS), currently underdevelopment (VandenPlas et al., 'Development of the Brussels Infant and Toddler Stool Scale ('BITSS"): Protocol of the study', BMJ Open 2017; 7:e014620.).

If for example the BSS is used, the vector is a $1 \times 1 \times 7$ vector comprising probabilities for each of the seven possible scores which form the scale.

The step 304 may be performed by a controller of the portable device 10, or may be performed by a server in communication with the portable device 10. In the second scenario, the controller of the portable device will instruct a transceiver of the portable device 10 to transmit the captured image to a server, and the processing of the captured image, that is, the computing of the CNN to provide a classification vector, and/or a predicted score, is performed by the server. This is suitable when the portable device lacks sufficient computational and graphical power to perform the operations required by the CNN. After the classification vector has been obtained by either the server or the portable device 10, step 305 consists of storing information about the classification vector or about the score. This information may be stored in the portable device 10 or in the server, or in both. If information about the classification vector is stored, the portable device may then make a decision of the most likely score by selecting the score with the highest probability value among the scores in the classification vector. If the score is stored, the step of making a decision may be omitted. This score is then displayed by the portable device 10 executing the application. In another embodiment, the server may also perform the selection of the score based on the probability values of all the scores, and send the score to the portable device. The information about the predicted score comprises at least one of the score itself, the captured image, information about a date and/or time at which the image was captured, the classification vector obtained with the CNN, or some additional information which may be useful for the parents and caregivers and for the app.

Figure 4:
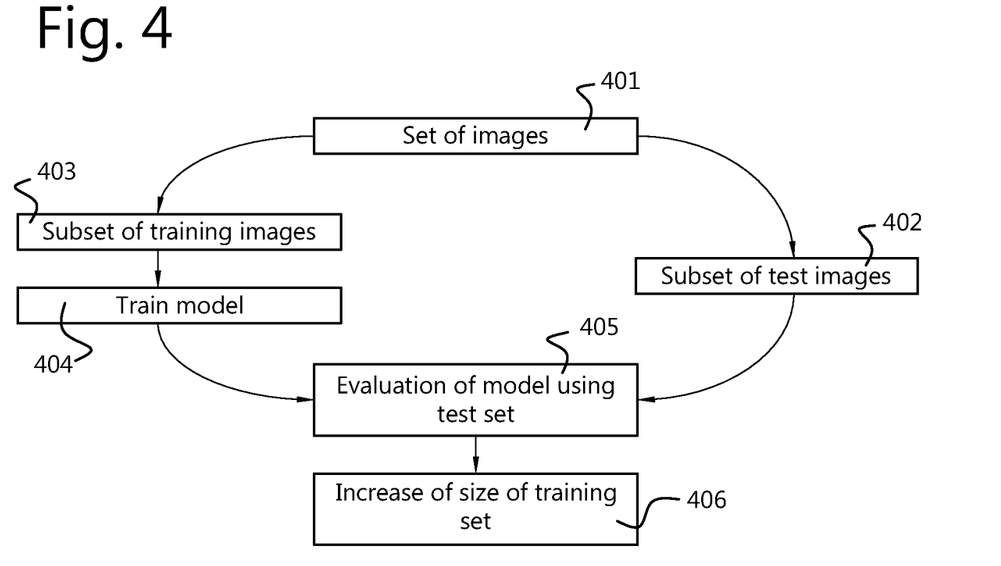
FIG. 4 illustrates a diagram of the training of images according to the present invention.

FIG. 4 illustrates a diagram of the training of images according to the present invention. When the app for providing information about a stool is being executed in the portable device 10, the captured image is input to a model comprising a CNN which will provide as a result a classification vector comprising probability values for the possible scores within a stool analysis scale, or a predicted score from said classification vector. In order to provide the classification vector, the CNN needs to be previously pre-trained, that is, it needs to be provided with enough information to be able to classify an input image. This may be performed with a set of labeled images (labeled with a score of a stool analysis scale), so that from the set of labeled images, the CNN can learn to automatically predict a specific label. Transfer learning may also be used in order to answer a specific image recognition task (like predicting a score of a BSS or BITSS from picture of a stool). This methodology allows building a model that will answer a specific question without collecting thousands of pictures and training a model from scratch. In this approach, a pre-trained model may be used and only the last layers are customized in order to predict the score. The CNN to be used may be based on known CNNs (for example based on Tensorflow libraries), but at least the last layer is customized, so that the output of the CNN provides a classification vector containing each of the scores of a stool analysis scale. The training of the at least last layer of the CNN is performed as follows. In step 401, an initial set of images is provided. Examples of a suitable set size are at least 200 images per score, at least 1000 images in total (comprising the images for all the scores of the scale), more preferably at least 1500, and more preferably at least 1600 images. These images are manually labeled with one score of the stool analysis scale to be used, such as the BSS. Among the initial set of images, a subset is selected in step 402 as test images, and a subset is selected in step 403 as training images. With the subset of training images, in step 404 the train model is implemented, and during the train model, the values given to certain elements in the operations being performed are updated by comparing the operation results with the labels that the images initially have. In that way, the CNN "learns" how to better predict the right score for an image. After that, the subset of test images is used to evaluate the model in step 405. Once this iteration is done, step 406 may be optionally performed, wherein the size of the training set may be increased (and therefore the size of the test set is decreased) and the iteration process is repeated from step 401. This fine tuning step 406 may increase the accuracy of the model. Once the CNN is trained, the values it uses for the elements in the different operations are known, and with them the CNN is able to predict the classification of an input image, such that an image of a stool in a diaper captured by a portable device. The trained model comprising the CNN may then be run in the portable device, or in the server, to provide a score for a captured image, as already illustrated above. According to embodiments of the invention, additionally to the fine tuning step 406, the app may allow to collect additional images to be used for retraining the model, if the initial data set is not adequate enough to reach an acceptable accuracy.

During the training step, and in order to improve the accuracy and reliability of the classification, a step can be performed in which, for the manual labelling of the images, assessment is given by at least one, preferably two, parents or caregivers (for example mothers), wherein these parents or caregivers preferably have no relation with the infants from which the initial set of images was obtained. In a preferred embodiment, where the assessment of two parents or caregivers (or a combination) is used, disagreement in their assessment is solved by the assessment of a healthcare professional in order to obtain the final score, that is, label.

In an example according to an embodiment of the present invention, a total of 2731 images is used as the initial set of images. Among these images, a subset of 2478 images is selected as training images, and a subset of 209 images is selected as test images. The table 1 below shows an example of an evaluation performed with the 209 test images:

TABLE 1

| | | Predicted stool consistency: machine learning | | | | | | |
|---|---|---|---|---|---|---|---|---|
| | | 1 | 2 | 3 | 4 | 5 | 6 | 7 |
| Predicted stool consistency: human | 1 | 16 | 5 | 0 | 0 | 0 | 0 | 0 |
| | 2 | 3 | 10 | 3 | 0 | 0 | 0 | 0 |
| | 3 | 1 | 4 | 23 | 5 | 1 | 0 | 0 |
| | 4 | 0 | 1 | 6 | 32 | 6 | 1 | 4 |
| | 5 | 0 | 0 | 3 | 7 | 22 | 11 | 2 |
| | 6 | 0 | 0 | 0 | 0 | 4 | 16 | 8 |
| | 7 | 0 | 0 | 0 | 0 | 0 | 1 | 14 |

As seen in table 1, from the 209 test images, 16 images were identified as pertaining to score 1 by both a human and a machine learning classification. Similarly, 10 images were identified as pertaining to score 2 by both the human and the machine learning classification, and the like, as seen in the cells in the diagonal of table 1. This represents a degree of agreement of 63.6%. This level of agreement is even higher if an error of ±1 score is considered, as shown in the cells adjacent to the diagonal elements in table 1, from which it can be seen that the agreement reaches a 93.8%.

According to embodiments of the present invention, the classification of the stool consistency that is provided by the app being run in the portable device or on a server follows the seven possible scores of the BSS.

In an embodiment according the invention, the portable device's operating system is iOS and/or Android. The app run in the portable device 10 which provides the classification of the stool may be as follows:

First, there may be a registration process. When the application is opened, a user is given the option of signing in or registering. If register is clicked in, a new screen may be displayed asking for a code (such as a one-time password (OTP) code). Once entered and validated by the system as available a new screen may be displayed requesting login credentials such as an email and a password. Afterwards, information about the infant may be introduced in a next screen (name, date of birth, gender).

Second, once the registration is complete, or once the user is signed in, a "home" screen may be displayed, with different types of information and options, including information about a "Stool module". Within the stool module, the user may be able to create a new entry, thereby being allowed to capture an image, as explained above, or to input a stored image which may have been captured before, or received by the portable device. According to an embodiment of the invention, the portable device may automatically capture the image when certain conditions are met. According to another embodiment, the application may display some kind of guidance so that the user can take a photo with good enough characteristics. This guidance may be a message such as "For the best quality image, be in a room with sufficient light, and try to capture only the stool (and diaper)". The skilled person however understands that this is merely an example, and other guidance messages may be displayed. The application will then, using the method disclosed above, display a score on a stool analysis scale (such as watery, soft, formed and hard based on, for example, the correspondence with the BSS), and information related to the score may be stored in the portable device. Also the captured image may be stored in the portable device. With a plurality of entries stored, development graphs may be created in order to allow to follow the changes in the stool consistency, and also in order to determine the frequency in which the stool is provided, which may provide additional information related to for example diarrhoea or constipation.

The entries may be modified and deleted. The entries may also be shared with a health database (server) shared with the infant's healthcare provider (HCP) so that if there is an indication given for need for special care, the portable device can warn the user to contact the HCP, who will then have quick access to the relevant information to allow faster decision making on the next steps.

It may be possible for the HCP to compare the predicted score with the actual image and to amend the score if needed. In an embodiment, such a corrected sample is entered automatically into a set of further training data, so that the model can be retrained to improve the accuracy.

All the images captured with the app may be stored in the portable device and/or on a remote server with which the mobile device may communicate, which will allow HCP to have access to the data and to assess the data of their patients if granted access rights.

Figure 5:
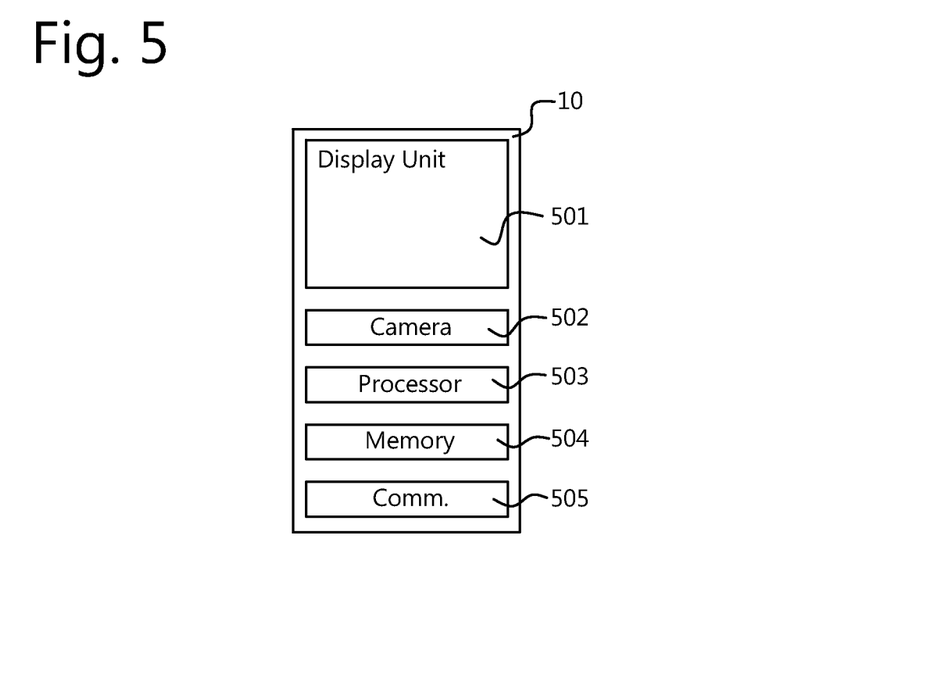
FIG. 5 schematically shows a portable device according to an embodiment of the present invention.

FIG. 5 schematically shows a portable device 10 according to an embodiment of the present invention. The portable device 10 has a display unit 501, which may be touch screen suitable for displaying information and handling user input. The device 10 further has a camera 502 for recording images and video clips, a processor 503 for processing recorded images, a memory 504 for storing images, program data, the CNN, and the like, and a communication unit 505 for communication with other devices over wired or wireless connections. In an embodiment the processor 503 is programmed to process recorded images using the CNN and to generally implement the processes as described in this application.

Figure 6:
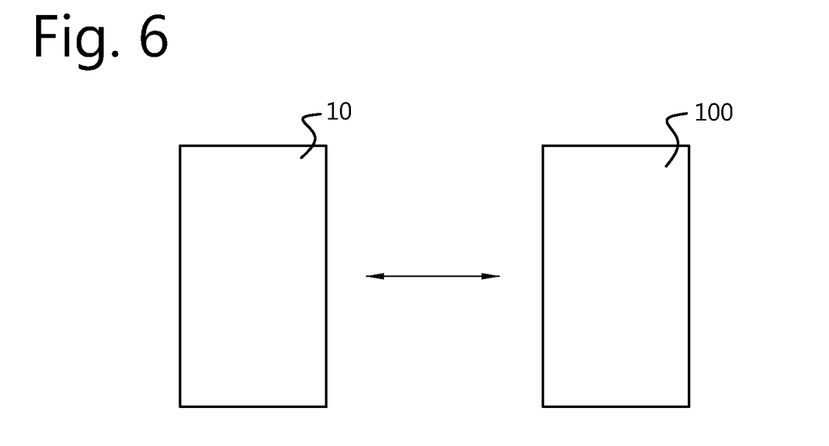
FIG. 6 schematically shows a portable device and a server according to an embodiment of the present invention.

FIG. 6 schematically shows a portable device 10 and a server 100 according to an embodiment of the present invention. The portable device 10 and server 100 can communicate over a wired or wireless link. In an embodiment, the portable device 10 sends recorded images to the server. The server has a processor, a memory, and a communication unit. The server 100 can be programmed to process received images using the CNN and to send back the results to the portable device 10. In addition, the server may store the obtained results and/or the received images and/or any intermediate calculation results. The server may be further arranged to implement the training method described in reference to FIG. 4.

In the foregoing description of the figures, the invention has been described with reference to specific embodiments thereof. It will, however, be evident that various modifications and changes may be made thereto without departing from the scope of the invention as summarized in the attached claims.

In particular, combinations of specific features of various aspects of the invention may be made. An aspect of the invention may be further advantageously enhanced by adding a feature that was described in relation to another aspect of the invention.

It is to be understood that the invention is limited by the annexed claims and its technical equivalents only. In this document and in its claims, the verb "to comprise" and its conjugations are used in their non-limiting sense to mean that items following the word are included, without excluding items not specifically mentioned. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention claimed is:

1. A computer-implemented method of analysing the consistency of stool, comprising the steps of:
   providing stool of an infant,
   capturing, with a portable device comprising a camera, an image of the stool, wherein the image is a colour image,
   providing the captured image to an input layer of a pre-trained convolutional neural network, CNN;
   processing the captured image using the CNN to obtain, from a final layer of the CNN, a classification vector and to obtain a predicted score from the classification vector;
   wherein at least the final layer of the CNN has been customized so that each element of the classification vector corresponds to a respective score of a stool analysis scale,
   wherein processing the captured image includes,
      detecting a colour of the stool,
      observing a stool pattern, wherein the stool pattern includes the detected colour of the stool,
   wherein each element of the classification vector includes a probability of the corresponding score of the stool analysis scale based on the observed stool pattern, and
   wherein the predicted score is a score of the stool analysis scale corresponding to the element of the classification vector with the highest probability,
      providing an indication, with the portable device comprising a display, based on the predicted score, that either everything is normal or that the stool is not behaving as expected, and
      storing the predicted score and the captured image.

2. The method according to claim 1, wherein the stool is provided in an open diaper.

3. The method according to claim 2, wherein the predetermined conditions comprise at least one of a condition that the diaper is placed on a surface with a regular background or a condition that the diaper is the only object present in the image.

4. The method according to claim 1, wherein the stool is provided in a potty, a bed pan, a toilet chair or a toilet with plateaus.

5. The method according to claim 1, further comprising displaying, by the portable device, guiding information to meet predetermined conditions before capturing the image.

6. The method according to claim 5, wherein the predetermined conditions comprise at least one of a condition that the stool is placed on a surface with a regular background or a condition that the stool is the only object present in the image.

7. The method according to claim 1, wherein capturing the image comprises automatically capturing the image by the portable device when predetermined conditions are met.

8. The method according to claim 1, wherein the information about the predicted score comprises at least one of the predicted score, the captured image of the stool, and the date and/or time at which the image was captured.

9. The method according to claim 1, wherein processing the captured image using the CNN is performed by the portable device.

10. The method according to claim 1, wherein processing the captured image using the CNN is performed by a server communicating with the portable device.

11. The method according to claim 1, wherein the information about the predicted score is stored in at least one of the portable device or a server communicating with the portable device.

12. The method according to claim 1, further comprising analysing a frequency in which the stool is produced, based on stored time information related to the predicted scores for a plurality of captured images.

13. Computer program product for analysing the consistency of stool, comprising:
   a non-transitory computer readable medium comprising codes executable by at least one processor to execute a method according to claim 1.

14. A system for analysing the consistency of stool, comprising:
   a portable device comprising:
      a camera configured to capture a colour image of a stool of an infant,
      a controller configured to
      provide the captured colour image to an input layer of a pre-trained convolutional neural network, CNN,
      detect a colour of the stool based on the captured colour image,
      observe a stool pattern, wherein the stool pattern includes the detected colour of the stool,
      obtain from a final layer of the CNN, a classification vector; wherein at least the final layer of the CNN has been customized so that each element of the classification vector corresponds to a respective score of a stool analysis scale,
      obtain information about a predicted score from the classification vector,
      wherein each element of the classification vector includes a probability of the corresponding score of the stool analysis scale based on the observed stool pattern, and
      wherein the predicted score is a score of the stool analysis scale corresponding to the element of the classification vector with the highest probability,
      provide and indication, via a display of the portable device, based on the predicted score, that either everything is normal or that the stool is not behaving as expected, and
      a memory for storing the predicted score and the captured image.

15. The system according to claim 14, wherein the stool is provided in an open diaper.

16. The system according to claim 14, wherein the stool is provided in a potty, a bed pan, a toilet chair, or a toilet with plateaus.

17. The system according to claim 14, wherein the information about the predicted score comprises at least one of the predicted score, the captured image of the stool, and the date and/or time at which the image was captured.

18. The system according to claim 14, further comprising a server for communicating with the portable device, wherein the server is configured to store the information about the predicted score.

19. The system according to claim 14, wherein processing the captured image using the CNN to obtain the classification vector from a final layer of the CNN is performed by the portable device.

20. The system according to claim 14,
wherein the server is further configured to process the captured image using the CNN to obtain the classification vector from a final layer of the CNN, and
wherein the portable device is further configured to transmit the captured image to the server and to receive the predicted score from the server.

* * * * *